(12) United States Patent
Nelson et al.

(10) Patent No.: US 9,125,845 B2
(45) Date of Patent: *Sep. 8, 2015

(54) DNA VACCINES, USES FOR UNPROCESSED ROLLING CIRCLE AMPLIFICATION PRODUCT AND METHODS FOR MAKING THE SAME

(75) Inventors: John Richard Nelson, Clifton Park, NY (US); Nichole Lea Wood, Niskayuna, NY (US); Brian Michael Davis, Albany, NY (US); Andrew Soliz Torres, Troy, NY (US)

(73) Assignee: General Electric Company, Niskayuna, NY (US)

( * ) Notice: Subject to any disclaimer, the term of this patent is extended or adjusted under 35 U.S.C. 154(b) by 677 days.

This patent is subject to a terminal disclaimer.

(21) Appl. No.: 13/077,231

(22) Filed: Mar. 31, 2011

(65) Prior Publication Data

US 2011/0206728 A1 Aug. 25, 2011

Related U.S. Application Data

(63) Continuation-in-part of application No. 12/169,993, filed on Jul. 9, 2008, which is a continuation-in-part of application No. 12/773,484, filed on May 4, 2010, now abandoned.

(51) Int. Cl.
| | |
|---|---|
| *A61K 39/00* | (2006.01) |
| *A61K 39/12* | (2006.01) |
| *A61K 39/02* | (2006.01) |
| *A61K 39/002* | (2006.01) |
| *A61K 39/145* | (2006.01) |

(52) U.S. Cl.
CPC .............. *A61K 39/00* (2013.01); *A61K 39/145* (2013.01); *A61K 2039/53* (2013.01); *C12N 2760/16134* (2013.01); *C12N 2760/16234* (2013.01)

(58) Field of Classification Search
None
See application file for complete search history.

(56) References Cited

U.S. PATENT DOCUMENTS

| | | | |
|---|---|---|---|
| 7,605,139 B2 | 10/2009 | Yu et al. | |
| 2002/0187952 A1* | 12/2002 | Palmer et al. | 514/44 |
| 2007/0122804 A1* | 5/2007 | Fu | 435/6 |
| 2010/0266695 A1 | 10/2010 | Segura et al. | |
| 2010/0273673 A1 | 10/2010 | Kim et al. | |

FOREIGN PATENT DOCUMENTS

| | | | |
|---|---|---|---|
| WO | WO 2004096288 | * | 11/2004 |
| WO | 2006063355 A1 | | 6/2006 |
| WO | 2007018744 A1 | | 2/2007 |

OTHER PUBLICATIONS

English translation of WO 2004096288, pp. 1-36.*
Ryushin Mizuta et al; "Atomic force microscopy analysis of rolling circle amplification of plasmid DNA"Received Mar. 4, 2003; pp. 175-181.

* cited by examiner

*Primary Examiner* — Sarvamangala Devi
(74) *Attorney, Agent, or Firm* — Jenifer E. Haeckl

(57) ABSTRACT

A method of eliciting an immune response in an organism comprising: providing an unprocessed rolling circle amplification (RCA) product; and administering an effective amount of the unprocessed RCA product to the organism to elicit the immune response, wherein the unprocessed RCA product is prepared from a circular nucleic acid template comprising at least one promoter sequence, and at least one target sequence. A vaccine comprising unprocessed RCA product is also provided and methods for making the same.

6 Claims, 5 Drawing Sheets

DNA VACCINES, USES FOR UNPROCESSED ROLLING CIRCLE AMPLIFICATION PRODUCT AND METHODS FOR MAKING THE SAME

CROSS REFERENCE TO RELATED APPLICATIONS

This application is a continuation-in-part of U.S. patent application Ser. No. 12/169,993, entitled "Unprocessed Rolling Circle Amplification Product", filed Jul. 9, 2008; and U.S. patent application Ser. No. 12/773,484, entitled "Nucleic Acid Delivery Vehicle and Uses Thereof", filed May 4, 2010, which are herein incorporated by references.

TECHNICAL FIELD

The invention relates generally to DNA replication and the use of an unprocessed (non-cleaved, non-circularized and non-supercoiled) rolling circle amplification (RCA) product. Such use comprises, for example, producing DNA-based vaccines, eliciting immune responses in organisms, and transfecting materials into living cells.

BACKGROUND OF THE INVENTION

RCA is employed in the replication of circularized DNA sequences. RCA products are used in DNA sequencing, cloning, library construction, probe generation and genetic screening. More recently, RCA products are employed in cellular expression, wherein cells are administered with naked DNA to produce an RNA or protein; and in DNA vaccination, wherein an organism is administered with naked DNA to produce an immunological response. In the case of DNA vaccination, rather than administering the pathogen itself (generally in a dead or disabled form so as to minimize any risk of actual infection), as in standard vaccinations, some portion of the pathogen's genome is administered and is then expressed by the organism in a manner sufficient to elicit an immune response. Because only a portion of the pathogen's genome is administered, there is little or no risk of actual pathogenic infection.

To date, DNA for cell transfection and DNA vaccines is produced using plasmid DNA. However, the use of plasmid DNA requires labor-intensive and expensive plasmid purification and increases the risk of contamination by extraneous bacterial components such as proteins, DNA, RNA, small molecules or purification reagents (e.g., ethidium bromide, chloroform, phenol, etc.). Any of these contaminants may have undesirable consequences.

Methods developed more recently employ cell-free RCA techniques. These techniques do not require plasmid purification and therefore reduce the risk of contamination, and are better suited for expression in cellular systems and therapeutic applications, such as DNA vaccines. However, to ensure sufficient uptake and expression in the DNA recipient, such techniques have, to date, required extensive post-amplification processing of the RCA product, wherein the product is broken into shorter units (monomers, dimers, trimers, etc.) and then circularized or supercoiled. Such processing is expensive and time intensive.

BRIEF DESCRIPTION OF THE INVENTION

The examples of the methods and vaccines of the invention overcome many of the deficiencies in the art. One or more of the examples of the methods of the invention are able to elicit immune responses using unprocessed RCA products that do not require post-amplification processing.

In one example, a method of eliciting an immune response in an organism comprises, providing an RCA product; and administering an effective amount of the RCA product to the organism to elicit the immune response, wherein the RCA product is prepared from a circular nucleic acid template comprising at least one promoter sequence and at least one target sequence.

In an embodiment of a vaccine of the invention, the vaccine comprises at least one RCA product suitable for administration to an organism, wherein the RCA product comprises at least one target sequence coding for an expression product capable of eliciting an immune response in the organism.

In another embodiment, a vaccine composition comprises at least one RCA product suitable for administration to an organism, wherein the RCA product comprises a tandem repeat nucleic acid sequence consisting essentially of a promoter sequence and a target sequence.

One example of a method for transfecting a cell comprises the steps of: providing an unprocessed RCA product; and transfecting the cell with the unprocessed RCA product.

BRIEF DESCRIPTION OF THE DRAWINGS

These and other features of embodiments of the invention will be more readily understood from the following detailed description of the various aspects of the invention taken in conjunction with the accompanying drawings that depict various embodiments of the invention, in which.

DETAILED DESCRIPTION OF THE INVENTION

Figure 1:
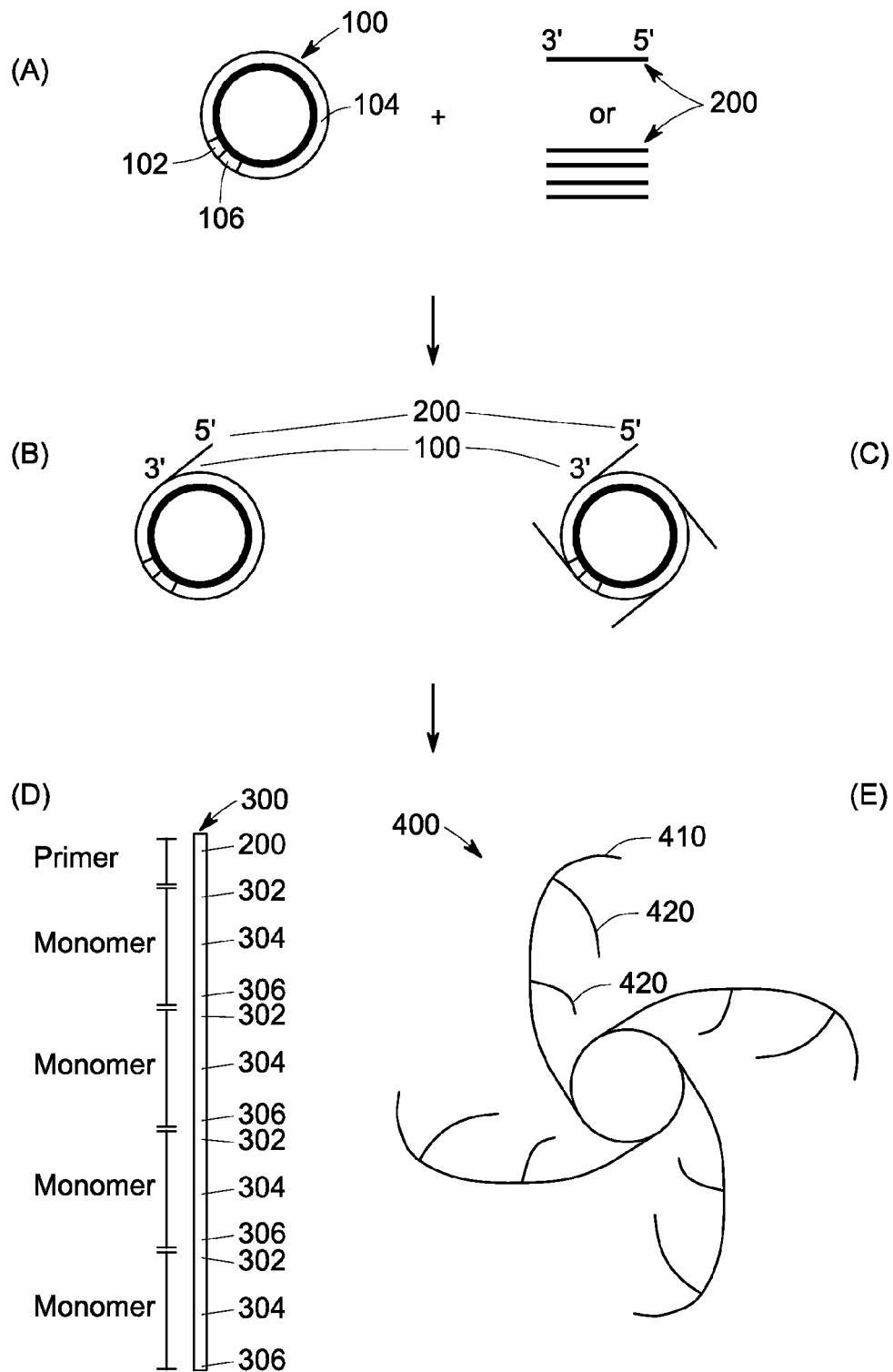
FIG. 1A to 1E are a schematic flow diagram of select stages of an illustrative method of producing an RCA product suitable for use according to aspects of the invention.

One or more examples of the methods relate generally to DNA replication and, with some of the examples, to the production and use of an unprocessed RCA product. The unprocessed RCA product may be transfected into a living cell, and the RCA-transfected living cells may be used for protein expression, cell therapy, or other research or medical uses. An illustrative use in protein expression comprises the expression of some signal (e.g. expression of a green fluorescent protein) useful in tracking a cell (e.g. during cell therapy). The unprocessed RCA products, when used in living cells, may be adapted for many different applications. In some examples, the unprocessed RCA product is used to elicit an immune response in an organism. Some examples relate to the use of an unprocessed RCA product in a DNA vaccine.

To more clearly and concisely describe and point out the subject matter of the claimed invention, the following definitions are provided for specific terms, which are used in the following description and the appended claims. Throughout the specification, exemplification of specific terms should be considered as non-limiting examples.

As used herein, "unprocessed" means not deliberately or intentionally cleaved, circularized, and/or supercoiled. The unprocessed RCA product is not processed down to monomers or single copy size (for example, using a restriction enzyme or using a recombinase), nor it is circularized to generate a circular form of RCA product or a plasmid.

As used herein, "operably linked" refers to a connection between a target sequence codes for a polypeptide, a transcriptional controlling sequence, and a translational controlling sequence in such a way to permit the expression of the polypeptide, when the transcriptional activation molecules are bound to the regulatory sequences.

As used herein, "target sequence" refers to a sequence that codes for an expression product, which may be able to elicit an immune response in an organism. The 'target sequence' may also be recognized as an 'expression sequence'. For example, the target sequence codes for a surface antigen of the bacterium, virus, fungus, parasitic organism, or non-parasitic organism from which it is derived.

As used herein, "pharmaceutically acceptable carrier" refers to encompass any carrier, which does not interfere with effectiveness of the biological activity of the active ingredient (for example, DNA, in case of DNA vaccine) and that is not toxic to the host to which it is administered. More specifically, the carrier assists in cellular uptake of nucleic acids (such as DNA) in case of a vaccine. For example, calcium ion may act as a pharmaceutically acceptable carrier used for better cellular uptake of DNA. The nucleic acid vaccines used for human have the final nucleic acid product in a pharmaceutically acceptable carrier, such as a buffered solution known in the art.

In some examples, a method of eliciting an immune response in an organism comprises providing an unprocessed RCA product; and administering an effective amount of the unprocessed RCA product to the organism to elicit the immune response, wherein the unprocessed RCA product is prepared from a circular nucleic acid template comprising at least one promoter sequence and at least one target sequence.

The circular nucleic acid template used for RCA may be selected from a group consisting of: double-stranded DNA (dsDNA), single-stranded DNA (ssDNA), and RNA. In some examples, the circular DNA template is an expression plasmid containing a sequence needed for replication and selection in host bacterial cells, in addition to the target sequence. This sequence may be used to enable the initial creation of the recombinant DNA circular construct that may be subsequently used as a template for prepared or bulk amounts of DNA by RCA.

In some examples, the circular nucleic acid template comprises a promoter sequence and at least one target sequence. In some examples, the circular nucleic acid template consists of a promoter sequence and at least one target sequence. Unlike plasmid DNA, which carry genes that provide resistance to various environmental conditions (such as antibiotics resistance genes), the circular nucleic acid template or the resulting unprocessed RCA product generally does not comprise such sequences. The absence of antibiotic resistance gene sequence, a termination sequence or an origin of replication (which are necessary in bacteria) in the circular nucleic acid template results in a nucleic acid comprising minimum non-coding sequences, and may be termed a 'minimal circle' which comprises a promoter and at least one target sequence. Therefore, the unprocessed RCA product formed from the circular nucleic acid template of such example has higher specific activity and is desirable for administration to an organism and as a vaccine.

In one example, the circular DNA template may include one or more promoters and at least one target sequence. In one example, the circular DNA may further comprise a termination sequence. Depending on the starting nucleic acid template, the amplified RCA product may comprise one or more recombination sites. In some examples, the unprocessed RCA product comprises a tandem repeat nucleic acid sequence. The unprocessed RCA product DNAs or RNAs often comprises tandem repeat sequences.

As noted, in some examples, the circular nucleic acid template comprises at least one promoter sequence, and at least one target sequence. In some other examples, the circular nucleic acid template comprises at least one promoter sequence, and at least two target sequences coding for different expression products. In one embodiment, each expression product is capable of eliciting an immune response in a host organism. In other examples, at least one target sequence codes for an expression product, which is capable of eliciting an immune response in a host organism, and the other target sequence may code for a protein-adjuvant. In some embodiments, the circular nucleic acid template may further comprise a termination sequence.

In one embodiment, the circular nucleic acid template consists essentially of a promoter sequence and at least one target sequence. The target sequence may code for an antigenic protein or peptide. In another embodiment, the circular nucleic acid template consists essentially of at least two target sequences coding for different expression products with at least one expression product being capable of eliciting an immune response in a host organism, for example, an antigenic protein or peptide. In this embodiment, the other target sequence may code for an adjuvant, which facilitates eliciting the immune response in the host organism. In some embodiments, the circular nucleic acid template may further comprise a termination sequence.

FIG. 1 shows a schematic flow diagram of selected stages of an illustrative method of producing an RCA product. In (A), a circular DNA template 100 (which may be single-stranded or double-stranded), including a promoter sequence 102, a target sequence 104 and a termination sequence 106, is combined with one or a plurality of oligonucleotide primers 200. While described here as employing a DNA template, some of the methods may similarly employ an RNA template. Target sequence 104 may be any DNA sequence, the replication of which is desired. Typically, the target sequence 104 is derived from a bacterium, a virus, a fungus, a parasitic organism, or a non-parasitic organism and will code for an expression product (e.g., a protein, such as a surface antigen) that is capable of eliciting an immune response in an organism, if that organism were to be exposed to the bacterium, virus, fungus, parasitic, or non-parasitic organism. In some examples, target sequence 104 codes for a protein, a messenger RNA (mRNA) sequence, a non-coding RNA sequence, a micro RNA (miRNA) sequence, a small interfering RNA (siRNA) sequence, or a monoclonal antibody (mAb) chain (heavy or light chain).

In some examples of the invention, the circular DNA template 100 may include multiple promoter, target and termination sequences. In such a case, target sequences for different strains of the same bacterium or virus may be transferred to a host cell or organism. Alternatively, entirely unrelated target sequences may be transferred in the same unprocessed RCA product. Such examples may be desired in which the unprocessed RCA product is to be used in a DNA vaccine, enabling vaccination against multiple strains and/or diseases in a single vaccine.

The target sequence codes for a surface antigen of the bacterium, virus, fungus, parasitic organism or non-parasitic organism from which it is derived. In some other embodiments, the target sequence is a synthetic sequence and codes for an expression product capable of eliciting an immune response in an organism. In a synthetic sequence, the codon usage can be optimized by including essential codons required for coding the expression product. In some embodiments, the target sequence is derived from at least one of: a bacterium, a virus, a fungus, a parasitic organism and/or a non-parasitic organism, and codes for an expression product capable of eliciting an immune response in an organism. The synthetic sequence may also code for a surface antigen of a bacterium, virus, fungus, parasitic organism or non-parasitic organism.

The target sequence may code for an antigenic protein or peptide. The peptide may be of various lengths. The antigenic protein or peptide may undergo typical host cell modifications, such as, but not limited to, glycosylation and phosphorylation. In one embodiment, the target sequence may code for a full-length antigenic protein or peptide, or in an alternate embodiment, the target sequence may code for a truncated antigenic protein or peptide. In some embodiments, the protein is a recombinant protein.

As shown in FIG. 1, at least a portion of the sequence(s) of oligonucleotide primers 200 is complementary to a portion of the sequence of circular DNA template 100. In some embodiments, the complementary portion of the oligonucleotide primer sequence is located at the 3' end of the primer while a non-complementary portion of the sequence is located at the 5' end. Such a primer may aid in displacement of the primer during RCA. RCA reactions require a primer and RCA reactions can be initiated by either added oligonucleotide primer(s) or primer(s) synthesized in the RCA reaction. Such synthesized primers may be generated using primase in the RCA reaction.

In FIG. 1 (B), a single oligonucleotide primer 200 is shown annealed to the circular DNA template 100. Such annealing occurs when a single species of primer is used, each primer having the same sequence, which is complementary to only a single portion of the circular DNA template 100. Alternatively, as shown in FIG. 1 (C), a plurality of primer species may be employed, the plurality including sequences complementary to more than one portion of the circular DNA template 100. As shown in FIG. 1 (C), four primers 200 are used, each having a sequence complementary to a different portion of the circular DNA template 100. In examples in which multiple species of primers are used, such primers may be specifically designed to include sequences complementary to a portion of the circular DNA template 100 or may include random DNA sequences. Commercially-available amplification kits, such as the TempliPhi™ Amplification Kits, available from GE Healthcare, may also be employed.

Replication of the circular DNA template 100 continues, with the DNA polymerase displacing the newly replicated, single-stranded DNA from the circular DNA template 100. The result is a linear concatemer of the sequence of the circular DNA template 100. Primers bind to the displaced single-stranded DNA and complete the double-stranded RCA product.

Any number of polymerases may be used in RCA. Among the more commonly used DNA polymerases are those exhibiting 3'-5' exonuclease activity, such as, for example, bacteriophage Phi29 DNA polymerase, Tts DNA polymerase, phage M2 DNA polymerase, bacterial DNA polymerase I (Pol I), the Klenow fragment of DNA polymerase I, bacterial DNA polymerase III (Pol III), T5 DNA polymerase, PRD1 DNA polymerase, T4 DNA polymerase holoenzyme, T7 DNA polymerase and Bst DNA polymerase I. Among these, bacteriophage Phi29 DNA polymerase is used in some embodiments. Polymerases not exhibiting 3'-5' exonuclease activity may also be used, including, for example, Taq polymerase, Tfl polymerase, Tth polymerase, eukaryotic DNA polymerase alpha and DNA polymerases modified to eliminate 3'-5' exonuclease activity.

In FIG. 1 (D), a double-stranded linear RCA product 300 is shown, as may be obtained by the annealing of a single species of primer, as in FIG. 1 (B). Linear RCA product 300 includes the primer sequence 200 and a plurality of monomers, linear copies of the sequence of circular DNA template 100 (e.g. repeating units of promoter sequence 302, target sequence 304 and termination sequence 306). Thus, linear RCA product 300 may serve as a template for the expression of multiple copies of the target sequence 304 once transcribed into mRNA and, optionally, translated into a protein.

The branched RCA product 400 in FIG. 1 (E) results from the multi-primed RCA shown in (C). Primary branches 410 are similar to linear RCA product 300, comprising a primer sequence 200 and multiple, repeating monomers of promoter sequence 302, target sequence 304 and termination sequence 306. Secondary branches 420 result from the annealing of a primer to the newly-replicated, single-stranded primary branch 410 during replication of the circular DNA template 100. While shown as a relatively simple branched structure, in practice, the RCA product produced by multi-primed RCA is likely to be much more complex than shown in (E), with branching continuing until the dNTPs are exhausted. Branched RCA product 400 is shown merely for purposes of illustration and to contrast with linear RCA products. The complex structure of the branched RCA products provide more stability and is less prone to the action of various exonucleases. The complex structure of the unprocessed RCA product protects the coding sequences present in the RCA product which further results in greater expression of the protein or peptide than with normal tandem repeated double stranded or single stranded DNA sequences.

Figure 2:
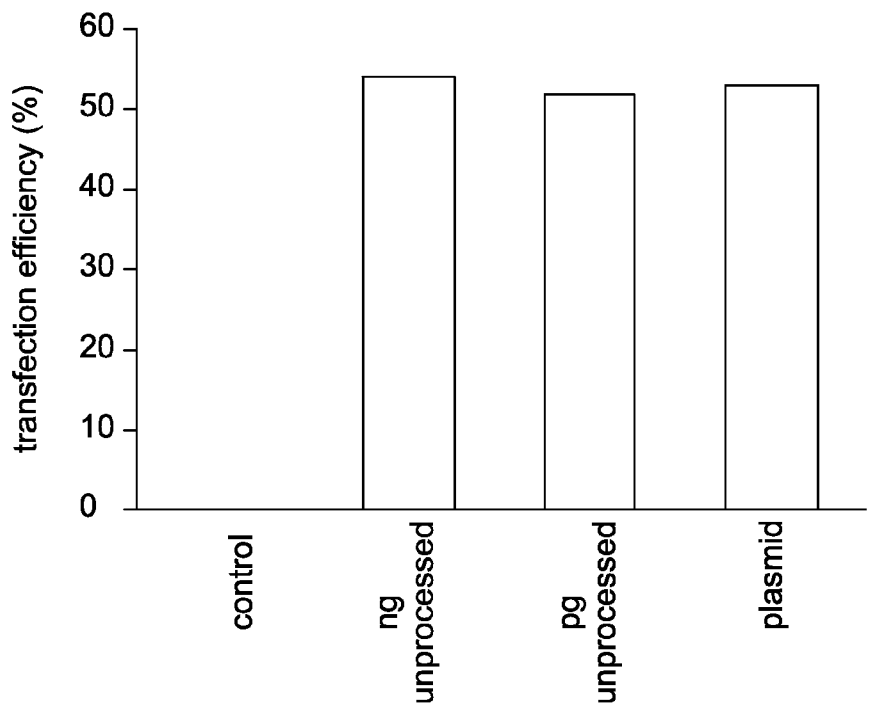
FIGS. 2-4 are graphs of the transfection efficiencies of unprocessed RCA product in comparison with plasmid RCA product.

Transfection of the unprocessed RCA product yields transfection efficiencies comparable with those of supercoiled plasmid DNA, the form of DNA commonly used for transfection of cells. For example, FIG. 2 shows the transfection efficiencies using equal amounts of DNA that has been amplified from 1.0 nanogram and 1.0 picogram quantities of initial supercoiled plasmid DNA (pHyg-EGFP) into RCA product (10,000-fold and 10,000,000-fold amplified, respectively) and that of an equal amount of supercoiled plasmid (pHyg-EGFP). The efficiencies of both "ng unprocessed," and "pg unprocessed" are equivalent to that of supercoiled plasmid where "plasmid" and "control" results represent untransfected cells. The results were consistent for eight independent examples.

Figure 3:
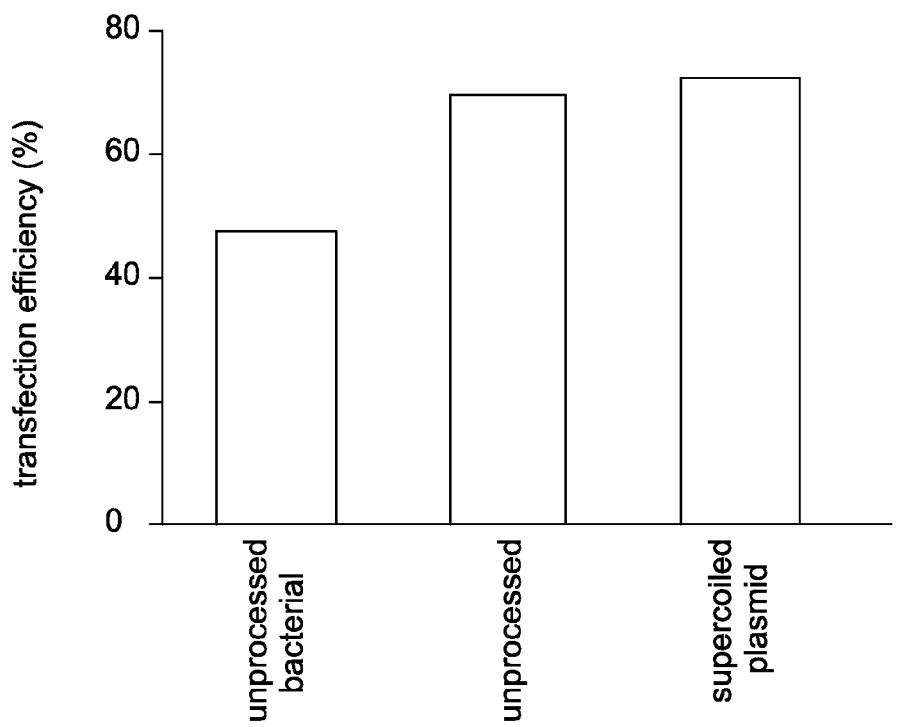

FIG. 3 shows the transfection efficiencies of unprocessed RCA product prepared from DNA amplified directly from pHyg-EGFP-transformed bacterial colonies containing the circular plasmid to be amplified, unprocessed RCA product prepared from a purified circular DNA template and supercoiled plasmid DNA. The unprocessed RCA product and supercoiled plasmid RCA product yielded similar transfection efficiencies (about 70%) and the unprocessed RCA product prepared from bacterial colony DNA yielded a transfection efficiency of approximately 48%.

Figure 4:
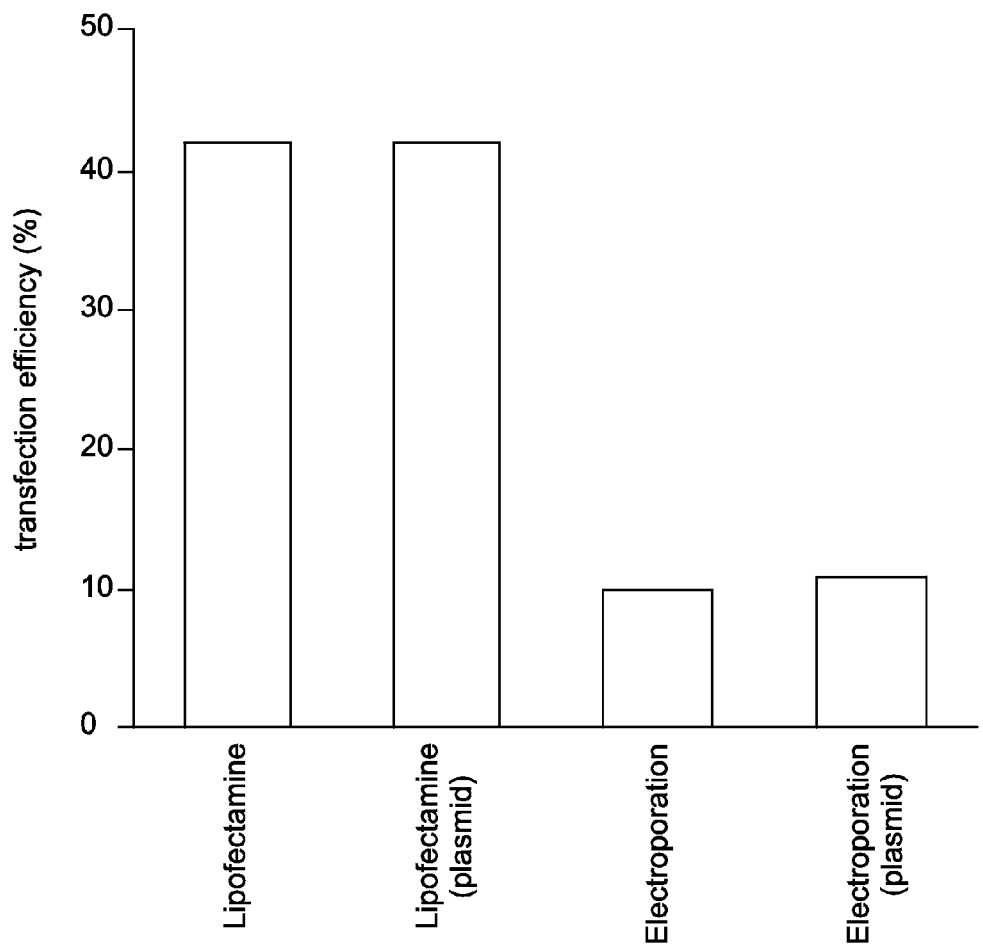

FIG. 4 shows the transfection efficiencies of unprocessed RCA product and plasmid DNA product using two common transfection techniques (lipofection using Lipofectamine™ and electroporation). Both techniques yielded very similar efficiencies, with lipofection performing better for both unprocessed RCA product and plasmid DNA product.

Figure 5:
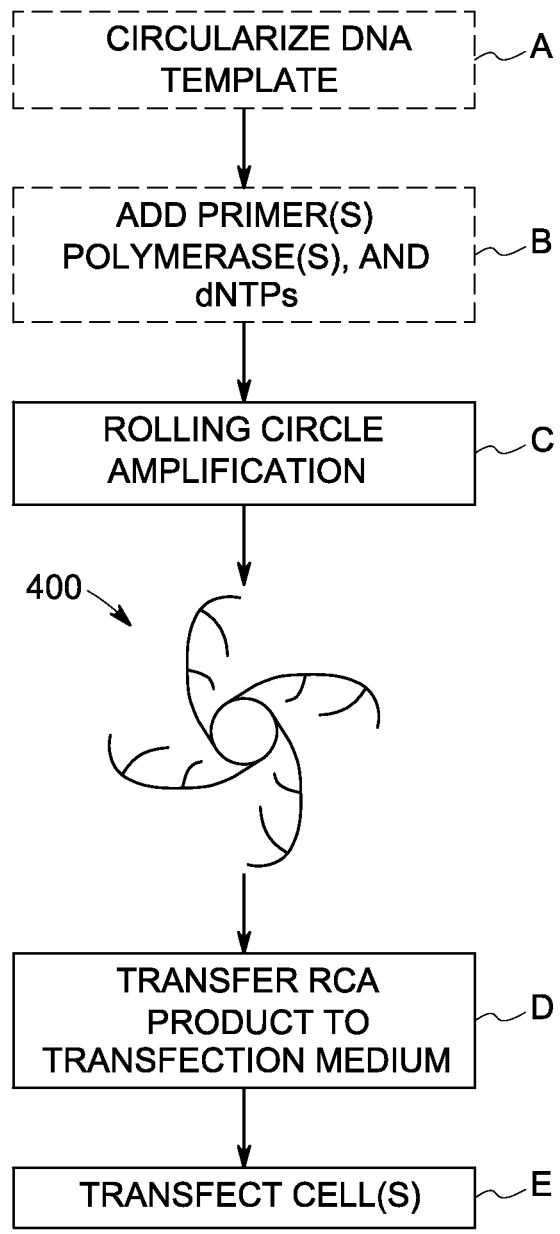
FIG. 5 is a flow diagram of an illustrative method of preparing and using unprocessed RCA product to transfect a living cell according to an embodiment of the invention.

FIG. 5 shows a flow diagram of an illustrative method for preparing and using unprocessed RCA DNA product. At A, the nucleic acid template (here, DNA) is circularized, if it is not so already. The DNA template may be a plasmid construct that may be created synthetically, or it can be created from purified components that are ligated or otherwise circularized together to form a circular construct. At B, one or more species of primer, one or more polymerases and deoxynucleotide triphosphates (dNTPs) are added to the circular DNA template. When the DNA template, primer(s), polymerase(s) and dNTPs are used in a pre-combined form, such addition may not be desired.

In some embodiments, modified nucleotides (e.g. non-natural nucleotides or nucleotide analogs, wherein one or more of the nucleotide's base, phosphate or sugar have been modified) may be used. Some of these may render their resulting DNA or RNA resistant to nuclease activity. Such non-natural nucleotides include, for example, phosphorothioated nucleotides, LNAs, dUTP, dITP, rNTP, 5-methyl dCTP, 2-amino-dATP, 2-thio-dTTP, 4'-thio-dTTP, 4'-thio-dCTP, and deaza-dGTP. Phosphorothioated nucleotides are used in some of the examples. At least a portion of the unprocessed RCA product may comprise modified nucleotides.

In known RCA methods, only the oligonucleotide primer(s) may comprise such modified nucleotides, as processing of the RCA product itself typically employs the use of nucleases to break the RCA product into monomeric subunits before their use. The use of the RCA product in its unprocessed form, however, is not subject to such limitation. Accordingly, the production of nuclease-resistant RCA product improves the product's overall stability and effectiveness, which may be important when the unprocessed RCA product is to be used in a DNA vaccine.

Modified nucleotides may also be used to alter the properties of the RCA product relative to RCA product from unmodified dNTPs. Certain nucleotide analogs may give better results in vivo. For instance, modified nucleotides may make an RCA product that is transcribed well in vivo. The RCA comprising nucleotide analogues is not used as a template by DNA recombination systems, which could be beneficial to prevent RCA product recombination into the cellular genome and force it to be retained as an extracellular transient element.

FIG. 5 further illustrates at C, that the circular nucleic acid template is replicated by RCA to yield an unprocessed RCA product 400. At D, the unprocessed RCA product 400 is transferred directly (e.g. without processing typical of RCA products, such as deliberate or intentional cleaving, circularization and/or supercoiling) to a suitable transfection medium. The transfection medium used will vary depending upon the transfection method chosen and the cells to be transfected. For example, the transfection medium may be a buffer, such as HEPES-buffered saline solution (HeBS). The transfection medium may also be a cationic polymer, such as DEAE-dextran or polyethylenimine. The transfection medium may also comprise any number of commercially-available products, such as Lipofectamine™, HilyMax, FuGENE®, JetPEI™, Effectene™, and DreamFect™. If the unprocessed RCA product is to be used as a DNA vaccine, the medium into which the unprocessed RCA product is transferred must be physiologically-acceptable, but may also comprise one or more adjuvants to augment the vaccinated organism's immune response. Unprocessed RCA products may also be delivered to a host cell or organism using a virus by 'transduction'.

Finally, at E, one or more cells are transfected with the unprocessed RCA product. For DNA vaccines, this may comprise the intramuscular injection of the unprocessed RCA product. Additional methods may be used to increase uptake efficiency. Such methods include, for example, dermal abrasion, electroporation, ultrasound, and particle-mediated projectile transfection. In the case of tissue culture cell transfection, this may comprise tissue culture cells either in suspension or adhered to a matrix. In one embodiment, a method of transfecting a cell comprises the steps of providing an unprocessed RCA product, and transfecting the cell with the unprocessed RCA product.

An example of a vaccine of the invention comprises at least one unprocessed RCA product suitable for administration to an organism, wherein the unprocessed RCA product comprises at least one target sequence coding for an expression product capable of eliciting an immune response in the organism. The RCA product used in the vaccine is produced at least in part from a nucleic acid template selected from a group consisting of: double-stranded DNA (dsDNA), single-stranded DNA (ssDNA), and RNA. In some embodiments, the RCA product comprises modified nucleotides as mentioned above.

In some embodiments, the unprocessed RCA product used as a vaccine comprises a tandem repeat nucleic acid sequence consisting essentially of a promoter sequence and a target sequence. The target sequence comprises a coding region that codes for a transcription factor. In some embodiments, the unprocessed RCA product consists of a tandem repeat nucleic acid sequence consisting essentially of a promoter sequence and a target sequence, wherein the target sequence comprises a coding region that codes for a transcription factor. The transcription factor may induce transcription of a gene that codes for a protein of interest, such as an antigen.

Some examples of the vaccine, which induces the expression of a gene that codes for a protein of interest, when introduced into an in vivo system (e.g. mammals, such as humans). The vaccine is a nucleic acid, which contains essential regulatory elements and upon introduction into an organism is able to direct the cellular machinery to produce the translational products (expression product), which is encoded by the target sequence. The expression product is capable of inducing the immune system of the organism and provides immunity. In one embodiment, the unprocessed RCA product consisting essentially of at least two target sequences coding for different expression products with at least one expression product being capable of eliciting an immune response in a host organism. In some embodiments, the target sequences may be operably linked to one or more transcriptional regulatory elements. Different transcriptional promoters, terminators, carrier vectors or specific gene sequences may be used for constructing the vaccine.

In some embodiments, the unprocessed RCA product DNA of vaccine may be unassociated with any proteins, adjuvants or other agents, which may affect the immune system of the host organism. In these embodiments, the RCA DNA is desirable to be in physiologically acceptable solution, such as, but not limited to, sterile saline or sterile buffered saline. In some other embodiments, the RCA product may be associated with liposomes or an adjuvant, to boost immune responses, such as a protein or other carrier. In some embodiments, various agents, such as, but not limited to calcium ions, may be used to assist cellular uptake of unprocessed RCA product as a vaccine. The agents, which assist in cellular uptake, are generally pharmaceutically acceptable carriers or excipients. It may be desirable for the nucleic acid vaccines intended for human use to have the final nucleic acid product in a pharmaceutically acceptable carrier or buffered solution.

In some embodiments, when the vaccine of the invention is introduced into a host organism, one or more proteins or peptides encoded by the target sequence may be produced and activated to develop a protective immune response in the host organism. Though the proteins or peptides encoded by the target sequence typically do not exist in the host organism, they are processed by the major histocompatibility (MHC) system. The proteins or peptides are processed by the organism, in a way analogous to when an actual infection occurs, as the proteins or peptides are produced by the host's own tissue. The inoculation of vaccines may result in the generation of significant protective immunity by helper T lymphocyte responses and activation of cytokines pathways. The vaccine may serve as a DNA vaccine for various diseases to activate the adaptive specific immune response, to generate B and T lymphocytes and/or natural killer cells against specific antigens associated with the disease. The DNA vaccine may comprise a target sequence codes for an immunogenically active component of a virus, such as an influenza virus and may be used to immunize a mammalian system by delivering the vaccine to the same. Similarly, a DNA vaccine may also be used to immunize against tumor-associated antigens, suppressing or attenuating tumor growth and treating cancers.

The immunization with a gene rather than its gene product may be more advantageous than nucleic acid vaccines. In such instance, when the antigen produced is native or nearly native, it can induce the potential immunogenic molecules to enter into the MHC class I pathway and evoke a cytotoxic T cell response. Another advantage of nucleic acid vaccines over conventional vaccines, is that they are able to induce protective cytotoxic T-cell responses, as well as helper T-cell and humoral immunity. Immunization with examples of nucleic acid vaccines of the invention, may elicit a cytotoxic T cell response as well as production of various cytokines. Instead of administering the whole genome of a pathogen, it is sufficient to elicit an immune response by administering only a portion of the pathogen's genome, which also minimizes risk for pathogenic infection.

The effective immunizing amount of the immunogenically active component encoded by the target sequence of the nucleic acid-vaccine may vary and may be any amount sufficient to evoke an immune response and provide immunological protection against a specific pathogen causing disease. The immunogenicity of nucleic acid vaccines is directly linked to cell transfection efficiency and the level of antigenic expression of proteins after delivery of nucleic acids and subsequent protein expression. The nucleic acids that are selected from RCA product increases gene expression in cells. Increasing either the amount of nucleic acids or the stability of the nucleic acids may induce higher level of expression of nucleic acids in cells. The amount of expressed DNA or transcribed RNA to be introduced into a vaccine recipient will have a very broad dosage range and may depend on the strength of the transcriptional and translational promoters used. In addition, the magnitude of the immune response may depend on the level of protein expression and on the immunogenicity of the expressed protein. In general, an effective dose ranges from about 1 ng to 1 mg of nucleic acid vaccine is administered directly into the tissue.

One or more examples of the nucleic acid vaccine of this invention may be administered or inoculated, subcutaneously, intramuscularly, intradermally or by other modes such as intraperitoneal, intravenous, or inhalation, in the presence of adjuvants or other substances capable of promoting nucleic acid uptake. The chosen route of administration will depend on the vaccine composition and the disease state of patients. In one embodiment, the nucleic acid vaccine may be administered intradermally, employing particle mediated epidermal delivery (PMED). The PMED technology is advantageous for administering vaccines, because the amount of DNA required is about 1000 times less than when injecting with a needle, which reduces the cost per dose of vaccine.

The following examples are intended to be illustrative of suitable methods for the production and use of unprocessed RCA products. Such methods are not the only methods suitable for use in the various aspects and embodiments of the invention and should not be viewed as limiting the scope of the invention.

Example 1

Production of an Unprocessed RCA DNA Product

Supercoiled DNA plasmid pHygGFP is prepared by standard methods at a concentration of 100 ng/microliter in TE buffer. An RCA reaction is assembled using 2.5 mL 2×R buffer (100 mM Tris:HCl, pH=8.2; 150 mM KCl; 20 mM $MgCl_2$, 0.02% TWEEN® 20, 2 mM DTT, 2 mM dNTP), 2.5 mL P buffer (10 mM Tris:HCl, pH=8.2; 0.5 mM EDTA; 0.01% TWEEN® 20; 0.08 mM random hexamer containing two phosphorothioate bonds at the 3' end), 0.1 mL of 1 mg/mL Phi29 DNA polymerase, and 250 ng supercoiled pHygGFP plasmid. The RCA reaction mixture is incubated at 30° C. for 16 hours to allow isothermal DNA amplification to occur and then heated at 65° C. for 20 minutes to inactivate the DNA polymerase.

The reaction may be assayed using PicoGreen® dye binding according to the manufacturer's instructions. Typical concentrations are approximately 0.6 mg/mL, representing a greater than 10,000-fold increase (i.e., from 250 ng to 3 mg).

Example 2

Production of an Unprocessed RCA DNA Product

An alternative method of producing unprocessed RCA DNA product, similar to that in Example 1, may be employed. Here, the reaction mix comprises:
  2.5 mL 2×R buffer;
  2.5 mL thioated random hexamer in TE buffer (final concentration is 40 μM primer);
  20 μL 100 mM dNTP;
  5 μL 1M DTT;
  50 μL 1M $MgCl_2$;
  100 μL 1 mg/mL Phi29 DNA polymerase; and
  250 ng pHygGFP supercoiled plasmid.

The reaction is incubated at 30° C. for 17 hours and then heated at 65° C. for 20 minutes to inactivate the enzyme. The reaction may be assayed using PicoGreen® dye binding according to the manufacturer's instructions.

Example 3

Preparation of Supercoiled Plasmid DNA

The supercoiled plasmid DNA in either of Examples 1 or 2 may be prepared as follows using the EndoFree Plasmid Giga Kit available from Qiagen.

Transformed DH5alpha bacteria carrying the pHygGFP plasmid are grown overnight in a fermentor at 37° C. in TB media. Bacterial cells are harvested by centrifugation at 6000×g for 15 min at 4° C. The bacterial pellet is resuspended in 125 mL of Buffer P1. 125 mL of Buffer P2 is added, mixed thoroughly by vigorously inverting 4-6 times, and incubated at room temperature for 5 min. 125 mL chilled Buffer P3 is added and mixed thoroughly by vigorously inverting 4-6 times. Mixing continues until white, fluffy material has formed and the Lysate is no longer viscous. The lysate is poured into a QIAfilter Giga Cartridge and incubated at room temperature for 10 min.

The vacuum source is activated and, after all liquid has been pulled through, deactivated. The QIAfilter Cartridge is left attached. 50 mL Buffer FWB2 is added to the QIAfilter Cartridge and the precipitate gently stirred using a sterile spatula. The vacuum source is activated until the liquid has been pulled through completely.

30 mL Buffer ER is added to the filtered lysate, mixed by inverting the bottle approximately 10 times, and incubated on ice for 30 min. QIAGEN-tip 10000 is equilibrated by applying 75 mL Buffer QBT, and allowing the column to empty by gravity flow. The filtered lysate is applied onto the QIAGEN-tip and allowed to enter the resin by gravity flow. The QIAGEN-tip is washed with a total of 600 mL Buffer QC.

DNA is eluted with 100 mL Buffer QN and precipitated by adding 70 mL (0.7 volumes) room-temperature isopropanol. The solution is mixed and centrifuged immediately at ≥15,000×g for 30 min at 4° C. The supernatant is carefully decanted and the DNA pellet washed with 10 mL of endotoxin-free room-temperature 70% ethanol (by adding 40 mL of 96-100% ethanol to the endotoxin-free water supplied with the kit) and centrifuged at ≥15,000×g for 10 min. The supernatant is carefully decanted without disturbing the pellet and the pellet air-dried for 10-20 min. The DNA is then re-dissolved in a suitable volume of endotoxin-free Buffer TE.

The reaction product may be quantified using UV absorption and PicoGreen® according to the manufacturer's instructions.

Example 4

Polyethylenimine Transfection of Unprocessed RCA DNA Product

Polyethylenimine (PEI) condenses plasmid DNA into positively charged particles that interact with the anionic surface of a cell. After entering the cell through endocytosis, the high charge density of the polymer causes lysosomal rupturing, releasing the DNA into the cytosol and permitting migration into the nucleus.

Unprocessed RCA product, such as that prepared in accordance with Example 1 above, may be used directly after amplification or after DNA precipitation and resuspension in an appropriate buffer.

Cells to be transfected (e.g., HEK 293) are grown following standard protocols to a concentration of up to about 3.5×$10^6$ cells/mL, preferably between about 5×$10^5$ cells/mL and about 1×$10^6$ cells/mL. Cells are preferably transfected during growth phase.

Cells are seeded at a concentration between about 1×$10^6$ cells/mL and about 2×$10^6$ cells/mL in half the target volume. Once brought to full volume, as described below, the density will be between about 0.5×$10^6$ cells/mL and about 1×$10^6$ cells/mL.

A DNA complex is prepared using 2.5 micrograms of DNA per mL of culture. A 1:3 ration of DNA to PEI (w/w) is combined in 150 mM NaCl at a volume equal to approximately 5% of the culture volume. A typical DNA complex for a 100 mL cell culture mix may comprise, for example, 0.5 mL 0.5 mg/mL DNA in TE, 1.17 mL 450 mM NaCl in TE, and 3.33 mL PEI. The complex is incubated for 10 minutes and added to the cell culture, approximately one hour after seeding. The combined culture is incubated for four hours and then brought to full volume by adding an equal volume of media.

The culture or media is harvested four to seven days post-transfection. In the case that the unprocessed RCA DNA product comprises the GFP gene, as in Example 1 above, the cells may be monitored in real time to assess GFP production. Alternatively, protein can be purified from the harvested cultures. Fluorescence activated cell sorting (FACS) analysis may also be performed.

Example 5

Transfection Efficiency of Amplified DNA

In one set, DNA has been amplified from 1.0 nanogram and 1.0 picogram quantities of initial supercoiled plasmid DNA (pHyg-EGFP) into RCA product (10,000-fold and 10,000,000-fold amplified, respectively) and the transfection efficiencies were measured (as shown in FIG. 2) using equal amounts of amplified DNA that of an equal amount of supercoiled plasmid (pHyg-EGFP). RCA was carried out for four hours at 30° C. using W+W+N*N*S primers (where + denotes a locked nucleic acid (LNA) backbone and * denotes a phosphothioate backbone). 100 ng of plasmid or unprocessed RCA product were then used for reverse transfection of 30,000 HEK 293 cells using Lipofectamine™ 2000. Two days after transfection, the cells were analyzed by flow cytometry and the percentage of GFP-positive cells were determined. The efficiencies of both 10,000-fold amplified RCA product ("ng unprocessed," approximately 54%) and 10,000,000-fold amplified RCA product ("pg unprocessed," approximately 52%) are equivalent to that of supercoiled plasmid ("plasmid," approximately 53%). "Control" results represent untransfected cells. Consistent results were obtained in eight independent studies.

In another set, the transfection efficiencies of unprocessed RCA product prepared from DNA amplified directly from pHyg-EGFP-transformed bacterial colonies containing the circular plasmid to be amplified was compared with the unprocessed RCA product prepared from a purified circular DNA template, and supercoiled plasmid DNA (as shown in FIG. 3). The transformed bacterial colonies were resuspended in 10 microliters of Luria broth. 0.5 microliter was then added to 9.5 microliters of GenomiPhi™ sample buffer, heated to 95° C. for two minutes and cooled to 4° C. on ice. 9 microliters of 2× reaction buffer and 1 microliter of phi29 enzyme mix was added and incubated at 30° C. for 90 minutes prior to heat inactivation at 65° C. for 10 minutes. As described above, 100 ng of plasmid or unprocessed RCA DNA were then used for reverse transfection of 30,000 HEK 293 cells using Lipofectamine™ 2000 and the percentage of GFP-positive cells determined two days later by flow cytometry. The unprocessed RCA product and supercoiled plasmid RCA product yielded similar transfection efficiencies of approximately 70% and approximately 72%, respectively. Even the unprocessed RCA product prepared from bacterial colony DNA, which allows for elimination of all plasmid DNA purification steps before transfection, yielded a transfection efficiency of approximately 48% (FIG. 3).

In another set, the transfection efficiencies of unprocessed RCA product and plasmid DNA product using two common transfection techniques (lipofection using Lipofectamine™ and electroporation) were determined (FIG. 4). Lipofection was carried out as described above. Electroporation was carried out using an Amaxa Nucleofector™ electroporator (buffer V, program Q01), electroporating 300 ng of unprocessed RCA DNA or supercoiled plasmid into $10^6$ cells. RCA DNA was electroporated in the TempliPhi™ reaction buffer and did not undergo buffer exchange to a low conductivity buffer. Two days after transfection, the percentage of GFP-positive cells was determined by flow cytometry. Both techniques yielded very similar efficiencies, with lipofection performing better for both unprocessed RCA product and plasmid DNA product as shown in FIG. 4.

Example 6

Vaccination with Unprocessed RCA DNA Induces Antibody and IFN-Producing T-Cells in Mice Influenza A and B viruses comprise two major surface glycoproteins, termed hemaglutinin (HA) and neuraminidase (NA). Antibody responses against HA are the primary mechanism of immune protection afforded by licensed killed vaccines. Influenza DNA vaccines encoding the HA gene of various subtypes have induced neutralizing antibody response and protection against influenza in mice and humans.

The RCA DNA and thioated RCA DNA were formulated onto gold beads for particle mediated epidermal delivery (PMED) and induced an immune response in mice that was equivalent or superior to that induced by the standard supercoiled plasmid DNA. The two RCA DNAs were precipitated onto 1 micron gold beads using the same standard spermidine-ethanol precipitation protocol routinely used for supercoiled DNA and delivered into mouse epidermis using the gene gun.

Figure 6A:
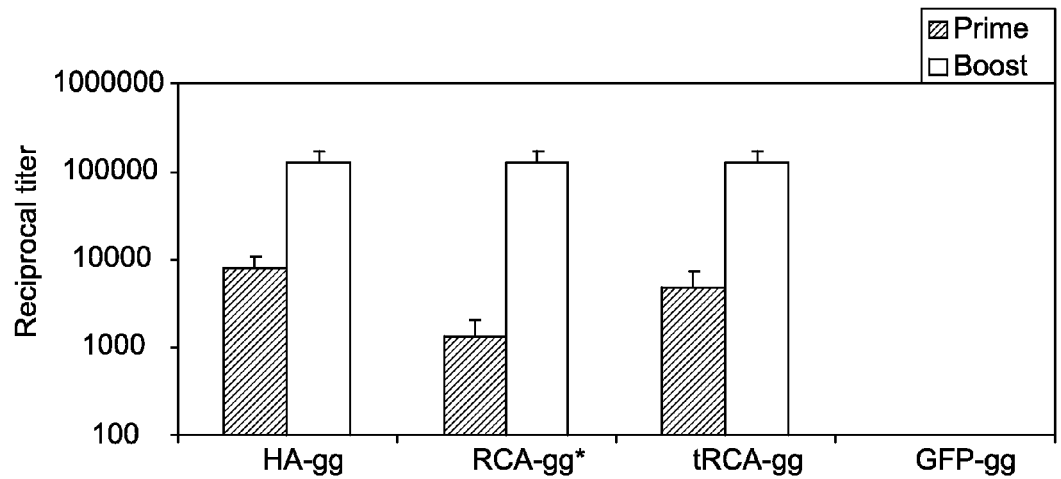
FIG. 6A is a graph showing a comparison of antibody response in cells induced with super coiled hemagglutinin (SC-HA) DNA, RCA DNA and tRCA DNA.

Groups of 4 Balb/c mice were immunized at weeks 0 and 4 with either the standard supercoiled influenza HA expression plasmid (sc-HA), the RCA and tRCA HA variants (RCA and tRCA, respectively), and a GFP expression plasmid (GFP) as a negative control. Sera from blood sampled at weeks four and six were analyzed for the presence of anti-HA antibodies by ELISA. Significant levels of antibody were detected in all groups at both time points, with post-boost levels indistinguishable between the groups (FIG. 6(a)).

Figure 6B:
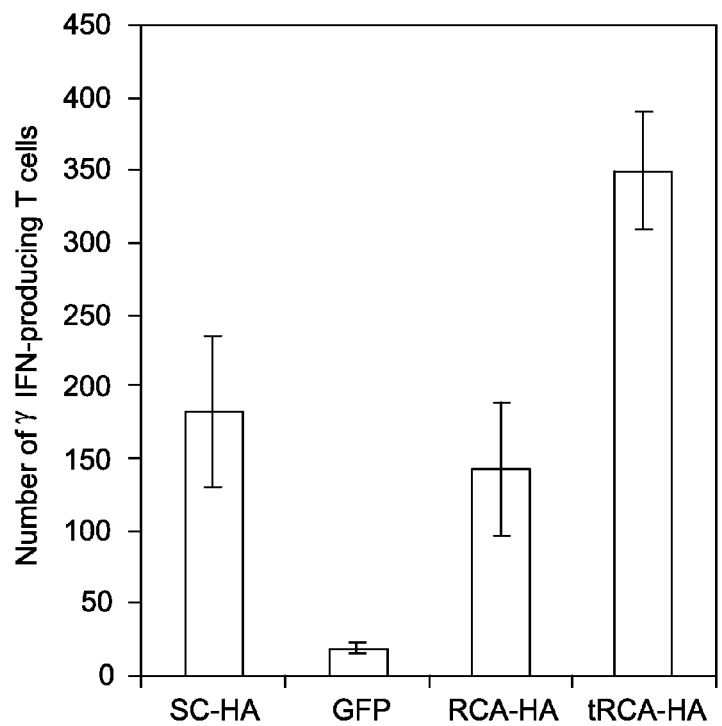
FIG. 6B is a graph showing a comparison of T-cell response in cells induced by vaccine comprising super coiled HA (SC-HA) DNA, GFP DNA, RCA DNA and tRCA DNA.

IgG antibody titers at the post-prime timepoint indicate a trend towards lower titers in the RCA groups, but this result is not statistically significant compared to the standard sc-HA DNA vaccine group. To determine the effects of RCA immunization on T cell responses, splenocytes were isolated from the mice at 2 weeks after the boost, stimulated with a HA-specific peptide pool representing the immunodominant region of the antigen and assayed for the presence of HA-specific T-cells producing γ-interferon (IFN) by ELISpot. A comparison of the responses induced in each vaccine group against this peptide is shown in FIG. 6(b). T cell responses induced in the unprocessed RCA group were indistinguishable from the standard SC group. However, mice receiving the thioated RCA (tRCA) DNAs showed a distinct 2-fold increase in the number of γ-IFN-producing T-cells. Equal amounts of total DNA were formulated onto the gold beads (2 μg/mg). Thus, the higher responses in the tRCA tend to show that thioated RCA DNA may be slightly less transient in vivo due to its resistance to exonuclease degradation. These results show that unprocessed RCA DNA can be readily formulated for PMED delivery and demonstrates that unprocessed RCA improves DNA vaccine potency.

The scope of the invention is defined by the claims, and may comprise other examples not specifically described that would occur to those skilled in the art. Such other examples are intended to be within the scope of the claims.

What is claimed is:

1. A method of eliciting an immune response to an antigen in a mammal comprising:
   providing an unprocessed rolling circle amplification (RCA) product and
   administering an effective amount of the unprocessed RCA product to the mammal to elicit the immune response to the antigen,
wherein the unprocessed RCA product is not deliberately or intentionally cleaved, circularized, and/or supercoiled and is prepared from a circular nucleic acid template comprising at least one promoter sequence and at least one target sequence, wherein the unprocessed RCA product comprises a tandem repeat nucleic acid sequence and the at least one target sequence codes for the antigen.

2. The method of claim 1, wherein the antigen is a surface antigen of a bacterium, a virus, a fungus, a parasite, or of a tumor-associated antigen.

3. The method of claim 1, wherein the at least one target sequence is a synthetic sequence.

4. The method of claim 3, wherein the synthetic sequence codes for the antigen.

5. The method of claim 1, wherein the circular nucleic acid template consists essentially of at least two target sequences each coding for a different antigen, wherein at least one antigen is capable of eliciting the immune response in the mammal.

6. The method of claim 1, wherein the circular nucleic acid template is selected from the group consisting of double-stranded DNA, single-stranded DNA, and RNA.

* * * * *